United States Patent [19]

Bank et al.

[11] Patent Number: 5,486,637

[45] Date of Patent: Jan. 23, 1996

[54] UNSATURATED ALCOHOLS AS ACCELERATORS FOR HYDROSILATION

[75] Inventors: Howard M. Bank, Freeland; Gary T. Decker, Midland, both of Mich.

[73] Assignee: Dow Corning Corporation, Midland, Mich.

[21] Appl. No.: 425,007

[22] Filed: Apr. 17, 1995

[51] Int. Cl.$^6$ ................................. C07F 7/08; C07F 7/18
[52] U.S. Cl. .............................................................. 556/479
[58] Field of Search ............................................... 556/479

[56] References Cited

U.S. PATENT DOCUMENTS

| | | | |
|---|---|---|---|
| 2,823,218 | 2/1958 | Speier et al. | 260/448.2 |
| 3,220,972 | 11/1965 | Lamereaux | 260/46.5 |
| 4,578,497 | 3/1986 | Onopchenko et al. | 556/479 |
| 5,359,111 | 10/1994 | Kleyer et al. | 556/479 |
| 5,359,113 | 10/1994 | Bank | 556/479 |
| 5,424,470 | 6/1995 | Bank et al. | 556/479 |

*Primary Examiner*—Paul F. Shaver
*Attorney, Agent, or Firm*—William F. Boley

[57] ABSTRACT

A hydrosilation process where a silicon hydride is reacted with an unsaturated reactant in the presence of a platinum catalyst and an accelerator selected from a group consisting of unsaturated secondary and tertiary alcohols and silated unsaturated secondary and tertiary alcohols. The accelerators are especially useful for the hydrosilation of unsaturated reactants where the unsaturation is in the internal portion of the reactant's structure, for example, as in cyclopentene and cyclohexene. The accelerators are believed to be effective in the presence or absence of oxygen.

22 Claims, No Drawings

UNSATURATED ALCOHOLS AS ACCELERATORS FOR HYDROSILATION

BACKGROUND OF INVENTION

The present invention is a hydrosilation process where a silicon hydride is reacted with an unsaturated reactant in the presence of a platinum catalyst and an accelerator selected from a group consisting of unsaturated secondary and tertiary alcohols and silated unsaturated secondard and tertiary alcohols. The accelerators are especially useful for the hydrosilation of unsaturated reactants where the unsaturation is in the internal portion of the reactant's structure, for example, as in cyclopentene and cyclohexene. The accelerators are believed to be effective in the presence or absence of oxygen.

It is known in the art to produce organosilicon compounds by reacting a silicon hydride containing compound with an unsaturated organic compound in the presence of a catalyst. This reaction is typically referred to as hydrosilation or hydrosilylation. Typically the catalyst is platinum metal on a support, a platinum compound generally in a solvent, or a platinum complex.

In Speier et al., U.S. Pat. No. 2,823,218, a method for the production of organosilicon compounds by reacting an Si-H with a compound containing aliphatic carbon atoms linked by multiple bonds in the presence of chloroplatinic acid is taught. Lamoreaux, U.S. Pat. No. 3,220,972, teaches a similar process, however the catalyst is a reaction product of chloroplatinic acid.

One of the major problems known in the art with hydrosilation reactions is the de-activation of the catalyst prior to the completion of the reaction. One method for reactivation of the catalyst has been to expose the reaction mixture to oxygen. For example, Onopchenko et al., U.S. Pat. No. 4,578,497, teach the use of an oxygenated platinum containing catalyst for use in hydrosilating alkylsilanes. Kleyer et al., U.S. Pat. No. 5,359,111, disclose a method for controlling hydrosilation reaction mixtures by controlling the solution concentration of oxygen in the reaction mixture, relative to the platinum present in the reaction mixture.

In addition to the problem of de-activation of the platinum catalyst, hydrosilation processes taught in the art are not particularly effective in hydrosilating internal unsaturated bonds in organic molecules. The present inventors have unexpectedly discovered that unsaturated secondard and tertiary alcohols and silated unsaturated secondard and tertiary alcohols can act as accelerators for platinum catalyzed hydrosilation processes. The accelerators are believed to improve yield of the process in the presence or absence of oxygen and are particularly effective in facilitating the hydrosilation of internal unsaturated bonds of organic molecules.

Bank et al., U.S. application Ser. No. 08/329,819, describe the use of unsaturated ketones as accelerators for hydrosilation.

SUMMARY OF INVENTION

The present invention is a hydrosilation process where a silicon hydride is reacted with an unsaturated reactant in the presence of a platinum catalyst and an accelerator selected from a group consisting of unsaturated secondary and tertiary alcohols and silated unsaturated secondary and tertiary alcohols. The accelerators are especially useful for the hydrosilation of unsaturated reactants where the unsaturation is in the internal portion of the reactant's structure, for example, as in cyclopentene and cyclohexene. The accelerators are believed to be effective in the presence or absence of oxygen.

DESCRIPTION OF INVENTION

The present invention is a hydrosilation process where a silicon hydride is reacted with an unsaturated reactant in the presence of a platinum catalyst and a novel accelerator. The hydrosilation process comprises: contacting
(A) a silicon hydride described by formula

where each $R^1$ is independently selected from a group consisting of alkyls comprising one to 20 carbon atoms, cycloalkyls comprising four to 12 carbon atoms, and aryls; each X is independently selected from a group consisting of halogen and organooxy radicals described by formula $-OR^1$, where $R^1$ is as previously described, a=0 to 3, b=1 to 3, and a+b=1 to 4; and
(B) an unsaturated reactant selected from a group consisting of
(i) substituted and unsubstituted unsaturated organic compounds,
(ii) silicon compounds comprising substituted or unsubstituted unsaturated organic substituents, and
(iii) mixtures of (i) and (ii);
in the presence of a platinum catalyst selected from a group consisting of platinum compounds and platinum complexes, and an accelerator selected from a group consisting of unsaturated secondard and tertiary alcohols described by formulas

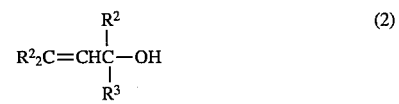

and

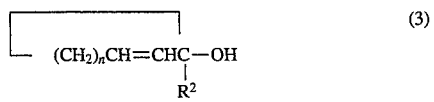

and silated unsaturated secondary and tertiary alcohols described by formulas

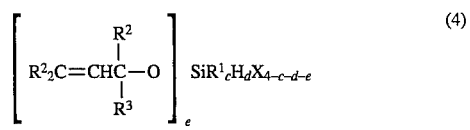

and

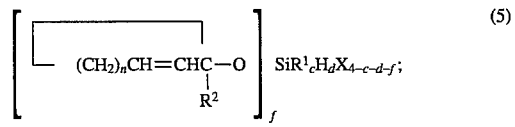

where each $R^2$ is independently selected from a group consisting of hydrogen and alkyls comprising one to six carbon atoms, each $R^3$ is an independently selected alkyl comprising one to six carbon atoms, c=0 to 3, d=0 to 3, c+d=0 to 3, e=1 to 4, f=1 to 4, and n=0 to 10.

The contacting of the silicon hydride with the unsaturated reactant can be effected in standard type reactors for conducting hydrosilation processes. The contact and reaction may be run as a continuous, semi-continuous, or batch reaction.

Silicon hydrides which are useful in the present process are described by formula (1), where each $R^1$ is independently selected from a group consisting of alkyls comprising one to 20 carbon atoms, cycloalkyls comprising four to 12 carbon atoms, and aryls; a=0 to 3, b=1 to 3, and a+b=1 to 4. $R^1$ can be a substituted or unsubstituted alkyl, cycloalkyl, or aryl as described.

In formula (1) it is preferred that each $R^1$ be independently selected from a group consisting of alkyls comprising about one to six carbon atoms. Even more preferred is when each $R^1$ is methyl.

In formula 1, each X is independently selected from a group consisting of halogen and organooxy radicals described by formula $—OR^1$ where $R^1$ is as previously described Preferred is when X is chlorine.

Examples, of silicon hydrides described by formula (1) which may be useful in the present process include trimethylsilane, dimethylsilane, triethylsilane, dichlorosilane, trichlorosilane, methyldichlorosilane, dimethylchlorosilane, ethyldichlorosilane, cyclopentyldichlorosilane, methylphenylchlorosilane, (3,3,3-trifluoropropyl)dichlorosilane, and methylmethoxychlorosilane. A preferred silicon hydride described by formula (1) is selected from a group consisting of methyldichlorosilane and dichlorosilane.

The silicon hydride is contacted with an unsaturated reactant selected from a group consisting of (i) substituted and unsubstituted unsaturated organic compounds, (ii) silicon compounds comprising substituted and unsubstituted unsaturated organic substituents, and (iii) mixtures of (i) and (ii). For purpose of this invention, "unsaturated" means that the compound contains at least one carbon-carbon double bond.

More specific examples of the unsaturated reactants useful in the present process include unsubstituted cycloalkene compounds comprising at least four carbon atoms, substituted cycloalkene compounds comprising at least four carbon atoms, linear alkene compounds comprising about two to 30 carbon atoms, branched alkene compounds comprising four to about 30 carbon atoms, and mixtures of two or more of any of the above.

The substituted and unsubstituted cycloalkene compounds useful in the present process are those containing one or more unsaturated carbon-carbon bonds in the ring. The unsubstituted cycloalkene compounds may be, for example, cyclobutene, cyclopentene, cyclohexene, cycloheptene, cyclooctene, cyclopentadiene, 1,3-cyclohexadiene, and 1,3,5-cycloheptatriene. Substituted unsaturated compounds useful in the present invention may be, for example, 3-methylcyclopentene, 3-chlorocyclobutene, 4-phenylcyclohexene, and 3-methylcyclopentadiene. The preferred cycloalkene compounds are cyclohexene and cyclopentene, with cyclohexene being the most preferred.

Other unsaturated organic compounds useful in the present process are linear and branched alkenyl compounds including, for example, compounds with terminal unsaturation such as 1-hexene and 1,5-hexadiene, compounds with internal unsaturation such as trans-2-hexene, and unsaturated aryl containing compounds such as styrene and α-methylstyrene.

The unsaturated reactants may also comprise halogen, oxygen in the form of acids, anhydrides, alcohols, esters, and ethers; and nitrogen. Two or more of the above described unsaturated organic compounds may be used in the present process.

The unsaturated organic compounds comprising halogen may include, for example, vinyl chloride, allyl chloride, allyl bromide, allyl iodide, allyl bromide, methallyl chloride, trichloroethylene, tetrachloroethylene, tetrafluoroethylene, chloroprene, vinylidene chloride, and dichlorostyrene.

Suitable unsaturated organic compounds comprising oxygen can include, for example, ethers such as allyl and vinyl ethers; alcohols such as allyl alcohol (vinyl carbinol), methylvinylcarbinol and ethynyldimethyl-carbinol; acids such as acrylic, methacrylic, vinylacetic, oleic, sorbic, and linolenic; and esters such as vinyl acetate, allyl acetate, butenyl acetate, allyl stearate, methylacrylate, ethylcrotonate, diallyl succinate and diallyl phthalate. Suitable nitrogen containing unsaturated organic compounds include, for example, indigo, indole, acrylonitrile, and allyl cyanide.

Specifically included within the definition of unsaturated organic compounds are those substituted by organofunctional moieties such as $CH_2=CHCH_2OC(O)C(CH_3)=CH_2$, $CH_2=CHCH_2NHCH_2CH_2NH_2$, $CH_2=CHCH_2NH_2$,

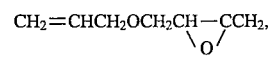

$CH_2=CHCH_2SH$ 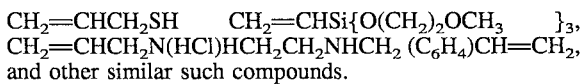
$CH_2=CHCH_2N(HCl)HCH_2CH_2NHCH_2$ $(C_6H_4)CH=CH_2$, and other similar such compounds.

The unsaturated organic compound can be a silicon compound comprising substituted and unsubstituted organic substituents as described by, for example, formulas $(CH_2=CH(CH_2)_g)_h R^1{}_i Si(OR^1)_{4-h-i}$ and $(CH_2=CH(CH_2)_g)_h R^1{}_i SiCl_{4-h-i}$, where $R^1$ is as previously described, g=0 to 12, h=1 to 3, i=0 to 3, and h+i=1 to 4.

Prior to contact of the silicon hydride with the unsaturated reactant, it may be preferable to treat or purify the unsaturated reactant. Methods useful for treating or purifying the unsaturated reactants are those known in the art for treating or purifying unsaturated organic compounds and include but are not limited to distillation and treatment with an adsorbent such as activated alumina or molecular sieves.

The relative amounts of silicon hydride and unsaturated reactant used in the present process can be varied within wide limits. Although one unsaturated carbon-carbon linkage per silicon bonded hydrogen atom is stoichiometric, there is no requirement that the process be run under stoichiometric conditions. Generally, it is preferred that the process be run with a stoichiometric excess of silicon hydride. Preferred is when the process is run with about 0.1 to ten percent stoichiometric excess of silicon hydride. However in some situations for safety reasons it may be preferred to run the process with an excess of unsaturated reactant, for example when the silicon hydride is dichlorosilane.

The silicon hydride and unsaturated reactant are contacted in the presence of a platinum catalyst selected from a group consisting of platinum compounds and platinum complexes. Any platinum containing material which effects the reaction between the silicon hydride and an unsaturated carbon-carbon bond of the unsaturated organic compound is useful in the present invention. Examples of platinum catalysts useful in the present process are described, for example, in Onopchenko et al., U.S. Pat. No. 4,578,497; Lamoreaux, U.S. Pat. No. 3,220,972; and Speier et al., U.S. Pat. No. 2,823,218 all of which are incorporated here by reference.

The platinum catalyst can be, for example, chloroplatinic acid, chloroplatinic acid hexahydrate, Karstedt's catalyst (i.e. a complex of chloroplatinic acid with sym-divinyltetramethyldisiloxane), dichlorobis(triphenylphosphine)platinum(II), cis-dichlorobis (acetonitrile)platinum(II), dicarbonyldichloroplatinum(II), platinum chloride, and platinum oxide.

A preferred platinum catalyst is selected from the group consisting of chloroplatinic acid, chloroplatinic acid hexahydrate, and platinum vinylsiloxane complexes such as a neutralized complex of chloroplatinic acid or platinum dichloride with sym-divinyltetramethyldisiloxane.

Generally, those concentrations of platinum catalyst which provide at least about one mole of platinum per billion moles of unsaturated carbon-carbon bonds added to the process by the unsaturated reactant may be useful in the present process. Concentrations of platinum catalyst providing as high as about one mole of platinum per one thousand moles of unsaturated carbon-carbon bonds added to the process by the unsaturated reactant may be useful. Higher concentrations of platinum may be used if desired. A preferred concentration of platinum catalyst is that providing about one to 1000 moles of platinum per $1 \times 10^6$ moles of unsaturated carbon-carbon bonds provided to the process by the unsaturated reactant.

The platinum catalyst may be dissolved in a solvent for ease of handling and to facilitate measuring the small amounts typically needed. Suitable solvents include, for example, non-polar hydrocarbon solvents such as benzene, toluene, and xylene and polar solvents such as alcohols, ketones, glycols, and esters.

The present process is carried out in the presence of an accelerator selected from a group consisting of unsaturated secondary and tertiary alcohols described by formulas (2) and (3) and silated unsaturated secondary and tertiary alcohols described by formulas (4) and (5). In the formulas, each substitutent $R^2$ is independently selected from a group consisting of hydrogen and alkyls comprising one to six carbon atoms. In addition to hydrogen, $R^2$ can be, for example, methyl, ethyl, propyl, butyl, and hexyl. Preferred is when $R^2$ is selected from a group consisting of hydrogen and methyl. In formulas (2) and (4), each $R^3$ can be an independently selected alkyl comprising one to six carbon atoms as described for $R^2$. Preferred is when $R^3$ is methyl. In formulas (4) and (5) it is preferred that $R^1$ be methyl.

In formulas (3) and (5), n can have a value of zero to 10. Preferred is when n is three. In the silated unsaturated secondary and tertiary alcohols described by formulas (4) and (5), c can have a value of zero to three, d can have a value of zero to three, and c plus d can have a value of zero to three. In formula (4), e can have a value of one to four. Preferred is when e has a value of one. In formula (5), f can have a value of one to 4. Preferred is when f has a value of one.

In formulas (4) and (5), each X is independently selected from a group consisting of halogen and organooxy radicals described by formula $-OR^1$, where $R^1$ is as previously described. Preferred is when X is a chlorine atom.

A preferred accelerator for use in the present process is selected from a group consisting of 2-methyl-3-buten-2-ol and silated 2-methyl-3-buten-2-ol (i.e. 2-trimethylsiloxy-2-methyl-3-butene).

An effective concentration of the accelerator is added to the present process, where an effective concentration is one that facilitates initiation of the reaction between the silicon hydride and the unsaturated organic compound, accelerates the rate of the reaction, or reduces loss of reactivity of the catalyst in the process. A useful effective concentration of the accelerator is generally within a range of about 0.01 to 20 weight percent of the weight of the unsaturated reactant. Preferred is when the accelerator is about 0.1 to ten weight percent of the weight of the unsaturated reactant. The accelerator may be added to the process as a pre-mix with the platinum catalyst or separately.

The temperature at which the present process can be conducted can generally be within a range of about $-10°$ C. to $220°$ C. It is preferred to conduct the process at a temperature within a range of about $15°$ C. to $170°$ C. The most preferred temperature for conducting the process is within a range of about $30°$ C. to $150°$ C.

The following examples are provided to illustrate the present invention. These examples are not intended to limit the claims herein.

Example 1. A variety of alcohols were evaluated for their ability to accelerate the reaction of methydichlorosilane with cyclohexene in the presence of a platinum catalyst.

A stock mixture was prepared in an argon purged and blanketed bottle. The stock mixture comprised four molar percent excess of methyldichlorosilane in cyclohexene which had been treated with 13X molecular sieves. About $3.7 \times 10^{-5}$ to $6 \times 10^{-5}$ moles of platinum, as a platinum divinylsiloxane complex, per mole of cyclohexene was added to the stock mixture. Aliquots of this catalyzed stock solution were then transferred to argon-purged glass tubes which contained alcohols as described in Table 1 at a concentration of one weight percent of the cyclohexene added to the tube. The tubes were heat sealed under argon purge and heated at $80°$ C. for three hours. At the end of three hours the tubes were cooled and the contents analyzed by gas chromatography using a thermal conductivity detector (GC-TC). The results of this analysis are reported in Table 1 as the normalized area percent of methyl(cyclohexyl)dichlorosilane ($MeC_HSiCl_2$) under the GC-TC trace minus the area of the cyclohexene as 100 percent. The results are given as the mean value for the number of runs indicated in parenthesis.

TABLE 1

Alcohols as Accelerators For Platinum Catalyzed Addition of $MeHSiCl_2$ to Cyclohexene

| Type Alcohol | Area % $Me(C_6H_{11})SiCl_2$ |
| --- | --- |
| None | 37.6 (7) |
| 2-Methyl-3-buten-2-ol | 93.5 (1) |
| Silated 2-methyl-3-buten-2-ol | 58.4 (1) |
| Allyl | 5.9 (2) |
| Trans-2-hexen-1-ol | 6.3 (4) |
| Hexyl | 5.5 (2) |

Example 2. The ability of unsaturated alcohols to accelerate the reaction of dichlorosilane with cyclopentene in the presence of a platinum catalyst was evaluated.

A stock mixture comprising about 14.2 weight percent dichlorosilane in cyclopentene was prepared in an argon purged and blanketed bottle. Aliquots of the mixture were transfered to argon purged glass tubes containing a platinum divinylsiloxane complex providing $7 \times 10^{-4}$ moles of platinum per mole of dichlorosilane. Unsaturated alcohol or silylated unsaturated alcohol providing about two weight percent based on total mass was then added to the tubes. The tubes were heat sealed under an argon blanket and heated at $120°$ C. for one hour. At the end of one hour the tubes were cooled and the contents analyzed by GC-TC. The results of the analysis are reported in Table 2 as the normalized area percent of cyclopentyldichlorosilane ($CpHSiCl_2$) and dicyclopentyldichlorosilane ($Cp_2SiCl_2$) under the GC-TC trace minus the area of the cyclopentene as 100 percent.

TABLE 2

Unsaturated Alcohols as Accelerators For Platinum
Catalyzed Addition of Dichlorosilane to Cyclopentene

| Type Alcohol | Area % CpHSiCl$_2$ | Area % Cp$_2$SiCl$_2$ |
|---|---|---|
| None | 56.9 | 0.0 |
| 2-Methyl-3-buten-2-ol | 52.8 | 5.3 |
| 2-Trimethylsiloxy-2-methyl-3-butene | 81.9 | 0.0 |

Example 3. The ability of 2-cyclohexen-1-ol to accelerate the reaction of methyldichlorosilane with cyclohexene in the presence of a platinum catalyst was evaluated. To an argon purged flask fitted with a mechanical stirrer and a condenser was added 78 g of cyclohexene which had been treated with 13X molecular sieves, 0.8 g of 2-cyclohexen-1-ol, and a platinum divinylsiloxane complex providing $1.4 \times 10^{-4}$ moles of platinum per mole of methyldichlorosilane. The mixture was heated under an argon purge to 80° C. and then about 104 g of methyldichlorosilane was added at a rate of about 2 ml per minute. During the addition of the methyldichlorosilane an exothermic reaction occurred raising the temperature of the reaction mixture to 98° C. After cooling, the content of the flask was analyzed by GC-TC and found to contain 91.2 area percent of cyclohexylmethyldichlorosilane.

We claim:

1. A hydrosilation process comprising: contacting (A) a silicon hydride described by formula

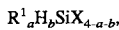    (1), where each $R^1$ is independently selected from a group consisting of alkyls comprising one to 20 carbon atoms, cycloalkyls comprising four to 12 carbon atoms, and aryls; each X is independently selected from a group consisting of halogen and organooxy radicals described by formula —OR$^1$, where $R^1$ is as previously described, a=0 to 3, b=1 to 3, and a+b=1 to 4; and (B) an unsaturated reactant selected from a group consisting of
  (i) substituted and unsubstituted unsaturated organic compounds,
  (ii) silicon compounds comprising substituted or unsubstituted unsaturated organic substituents, and
  (iii) mixtures of (i) and (ii);

in the presence of a platinum catalyst selected from a group consisting of platinum compounds and platinum complexes, and an accelerator selected from a group consisting of unsaturated secondard and tertiary alcohols described by formulas

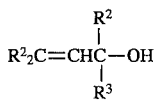

and

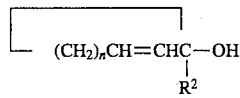

and silated unsaturated secondary and tertiary alcohols described by formulas

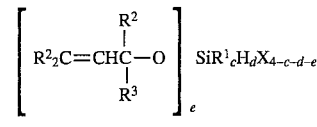

and

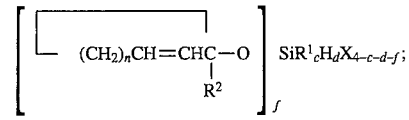

where each $R^2$ is independently selected from a group consisting of hydrogen and alkyls comprising one to six carbon atoms, each $R^3$ is an independently selected alkyl comprising one to six carbon atoms, c=0 to 3, d=0 to 3, c+d=0 to 3, e=1 to 4, f=1 to 4, and n=0 to 10.

2. A process according to claim 1, where each $R^1$ is independently selected from a group consisting of alkyls comprising about one to six carbon atoms.

3. A process according to claim 1, where $R^1$ is methyl.

4. A process according to claim 1, where X is chlorine.

5. A process according to claim 1, where the silicon hydride is selected from a group consisting of methyldichlorosilane and dichlorosilane.

6. A process according to claim 1, where the unsaturated reactant is selected from a group consisting of cyclohexene and cyclopentene.

7. A process according to claim 1, where about 0.1 to ten percent stoichiometric excess of silicon hydride is contacted with the unsaturated reactant.

8. A process according to claim 1, where the platinum catalyst is selected from a group consisting of chloroplatinic acid, chloroplatinic acid hexahydrate, and platinum vinylsiloxane complexes.

9. A process according to claim 1, where the platinum catalyst is a neutralized complex of chloroplatinic acid or platinum dichloride with sym-divinyltetramethyldisiloxane.

10. A process according to claim 1, where the platinum catalyst provides to the process about one to 1000 moles of platinum per $1 \times 10^6$ moles of unsaturated carbon-carbon bonds provided by the unsaturated reactant.

11. A process according to claim 1, where $R^2$ is selected from a group consisting of hydrogen and methyl.

12. A process according to claim 1, where $R^3$ is methyl.

13. A process according to claim 1, where n is three.

14. A process according to claim 1, where e is one.

15. A process according to claim 1, where f is one.

16. A process according to claim 1, where the accelerator is selected from a group consisting of 2-methyl-3-buten-2-ol and 2-trimethylsiloxy-2-methyl-3-butene.

17. A process according to claim 1, where the concentration of the accelerator is within a range of about 0.01 to 20 weight percent of the weight of the unsaturated reactant.

18. A process according to claim 1, where the concentration of the accelerator is within a range of about 0.1 to ten weight percent of the weight of the unsaturated reactant.

19. A process according to claim 1, where the silicon hydride is contacted with the unsaturated reactant at a temperature within a range of about 15° C. to 170° C.

20. A process according to claim 1, where the silicon hydride is contacted with the unsaturated reactant at a temperature within a range of about 30° C. to 150° C.

21. A process according to claim 1, where the silicon hydride is methyldichlorosilane, the unsaturated reactant is cyclohexene, about 0.1 to ten percent stoichiometric excess of silicon hydride is contacted with the unsaturated reactant, the accelerator is selected from a group consisting of 2-methyl-3-buten-2-ol and 2-trimethylsiloxy-2-methyl-3-butene, the concentration of the accelerator is within a range of about 0.1 to ten weight percent of the weight of the unsaturated reactant, the platinum catalyst is a neutralized complex of chloroplatinic acid or platinum dichloride with sym-divinyltetramethyldisiloxane, and the silicon hydride is contacted with the unsaturated reactant at a temperature within a range of about 30° C. to 150° C.

22. A process according to claim 1, where the silicon hydride is dichlorosilane, the unsaturated reactant is cyclopentene, the accelerator is selected from a group consisting of 2-methyl-3-buten-2-ol and 2-trimethylsiloxy-2-methyl-3-butene, the concentration of the accelerator is within a range of about 0.1 to ten weight percent of the weight of the unsaturated reactant, the platinum catalyst is a neutralized complex of chloroplatinic acid or platinum dichloride with sym-divinyltetramethyldisiloxane, and the silicon hydride is contacted with the unsaturated reactant at a temperature within a range of about 30° C. to 150° C.

* * * * *